(12) United States Patent
Chandwadkar et al.

(10) Patent No.: US 10,582,900 B2
(45) Date of Patent: Mar. 10, 2020

(54) OBJECT APPROACH DETECTION FOR USE WITH MEDICAL DIAGNOSTIC APPARATUS

(71) Applicant: KONINKLIJKE PHILIPS N.V., Eindhoven (NL)

(72) Inventors: Nikhil Rajan Chandwadkar, Nashik (IN); Mukund Dhondiram Dongare, Pune (IN); Shripad Anil Dharmadhikari, Best (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 176 days.

(21) Appl. No.: 15/575,695

(22) PCT Filed: May 20, 2016

(86) PCT No.: PCT/EP2016/061496
§ 371 (c)(1),
(2) Date: Nov. 20, 2017

(87) PCT Pub. No.: WO2016/188925
PCT Pub. Date: Dec. 1, 2016

(65) Prior Publication Data
US 2018/0289342 A1    Oct. 11, 2018

(30) Foreign Application Priority Data
May 28, 2015    (IN) .......................... 2676/CHE/2015

(51) Int. Cl.
*A61B 6/10*    (2006.01)
*H03K 17/955*    (2006.01)
(Continued)

(52) U.S. Cl.
CPC ............ *A61B 6/102* (2013.01); *A61B 5/1114* (2013.01); *A61B 5/6802* (2013.01);
(Continued)

(58) Field of Classification Search
CPC ..... A61B 6/102; A61B 5/1114; A61B 5/6802; A61B 6/4441; A61B 2562/0257; H03K 17/955; H03K 2017/9602
See application file for complete search history.

(56) References Cited

U.S. PATENT DOCUMENTS

| 5,570,770 A | 11/1996 | Baaten |
| 6,830,375 B2 | 12/2004 | Deshpande |

(Continued)

FOREIGN PATENT DOCUMENTS

| DE | 102007032533 A1 | 1/2009 |
| WO | 199719638 A1 | 6/1997 |

(Continued)

OTHER PUBLICATIONS

Smith, Joshua R. et al "Electric field imaging pretouch for robotic graspers", Intelligent Robots and Systems, 2007.

(Continued)

*Primary Examiner* — Courtney D Thomas

(57) ABSTRACT

An object approach detection apparatus (ACU) includes an input interface (IN) for receiving a response signal from a proximity sensor (PSj) measured relative to a first base-value of said at least one sensor. A filter module (FM) is configured to filter said response signal to produce a filtered response signal. A proximity event declarator (PED) is configured to declare a proximity event has occurred if the filtered response signal fulfils a first condition, in particular crosses a first threshold. A base value adaptor (BVA) is configured to choose a new base value in response of the declaring that the proximity event has occurred.

15 Claims, 6 Drawing Sheets

(51) Int. Cl.
 *A61B 6/00* (2006.01)
 *A61B 5/11* (2006.01)
 *A61B 5/00* (2006.01)
 *H03K 17/96* (2006.01)
(52) U.S. Cl.
 CPC ......... *A61B 6/4441* (2013.01); *H03K 17/955* (2013.01); *A61B 2562/0257* (2013.01); *H03K 2017/9602* (2013.01)

(56) References Cited

U.S. PATENT DOCUMENTS

| | | | |
|---|---|---|---|
| 2008/0122458 A1* | 5/2008 | Lenz | H03K 17/955 |
| | | | 324/687 |
| 2010/0061509 A1 | 3/2010 | D'Ambrosio | |
| 2011/0050256 A1 | 3/2011 | Frangen | |
| 2012/0035883 A1 | 2/2012 | Teissier | |
| 2014/0239982 A1 | 8/2014 | Alameh | |

FOREIGN PATENT DOCUMENTS

| | | |
|---|---|---|
| WO | 199739683 A1 | 10/1997 |
| WO | 2008070454 A2 | 6/2008 |

OTHER PUBLICATIONS

Schlegl, Thomas et al "Virtual Whiskers—Highly Responsive Robot Collision Avoidance", 2013 IEEE/RSJ International Conferencer on Intelligent Robots and Systems.

* cited by examiner

OBJECT APPROACH DETECTION FOR USE WITH MEDICAL DIAGNOSTIC APPARATUS

CROSS-REFERENCE TO PRIOR APPLICATIONS

This application is the U.S. National Phase application under 35 U.S.C. § 371 of International Application No. PCT/EP2016/061496, filed on May 20, 2016, which claims the benefit of IN Patent Application No. 2676/CHE/2015, filed on May 28, 2015. These applications are hereby incorporated by reference herein.

FIELD OF THE INVENTION

The invention relates to an object approach detection apparatus, to an imaging system, to a method of object approach detection, to a computer program element, and to a computer readable medium.

BACKGROUND OF THE INVENTION

The use of medical imaging equipment is prevalent throughout the medical field.

For instance, in interventions such as catheter introductions, X-ray imaging apparatuses of the C-arm type are sometimes used to obtain imagery of the patient's internal configuration to ensure proper localization of the catheter or other medical tool.

To get best results, images are acquired from a number of different viewing directions. To be able to do this, an X-ray source and/or detector of the imaging apparatus is mounted on a moveable gantry, also called a C-arm, which rotates round the patient to acquire the X-ray imagery. In some scenarios, these rotations are carried out whilst medical personnel is present close to the patient and/or close to the imaging apparatus itself.

It is not uncommon for collisions to occur, for instance, personnel is hit by the C-arm or surrounding equipment may be damaged if left inadvertently unsuitably placed in the C-arm's path.

To mitigate these situations some modern X-ray imagers use anti-collision systems. In these systems, proximity sensors are used to detect proximity of objects to the C-arm and a collision avoidance action is taken, such as the C-arm is slowed down or its motion is even brought to a halt.

Experience has shown however that performance of these anti-collision-systems under real conditions is often unsatisfactory. In particular, it has been observed that these systems sometimes produce an unacceptable number of "false positive" or "false negative" results: for instance the system fails to take the necessary collision avoidance action as it reached the conclusion that no object was present although there was. Or it happens that the system is overly cautious and hampers efficient use of the medical equipment. The anti-collision action is taken although there is no danger of collision. The system erroneously concluded that there was an obstacle although in reality there was not.

An exemplary imaging system with collision avoidance is described in Applicant's U.S. Pat. No. 5,570,770.

SUMMARY OF THE INVENTION

There may therefore be a need for alternative methods and systems for object approach detection in particular for use in a scenario where humans are working alongside work equipment with moveable parts.

According to a first aspect of the invention, there is provided an object approach detection apparatus, comprising:
an input interface for receiving a response signal from at least one proximity sensor measured relative to a first base-value of said at least one sensor;
a filter module configured to filter said response signal to produce a filtered response signal;
a proximity event declarator configured to declare a proximity event has occurred if the filtered response signal fulfils a first condition, in particular crosses a first threshold; and
a base-value adaptor configured to choose a new base-value in response of the declaring that the proximity event has occurred.

In other words, the apparatus allows interpreting sensor signals (such as capacitance values) in a novel way by resolving detection of object proximity into detection of proximity events and detection of proximity persistence. A frequency suppression methodology is used to distinguish valid proximity events and a "single-point", that is, instantaneous, base-value capture is used for establishing proximity event persistence. The system is also cable of differentiating between non-contact proximity and contact (eg physical touch), provided that a sufficient time interval exists between an object causing the proximity event and the actual touch event. The proposed system can use non-contact sensor technology (such as capacitive proximity sensor) and operate these for touch or non-touch event use. The apparatus thus helps eliminating the need for a separate hardware for additional collision safety to realize the contact-sensing.

"Object" should be construed broadly as physical objects (equipment, furniture, etc) but also animate objects, such as body parts of a human or animals. In particular, when the apparatus is used in an imaging apparatus with moving gantry, the object may relate to medical equipment arranged in the surrounding of the gantry or to body part (hand, leg, head etc) of the patient being imaged or of the medical personnel ("user") or of other bystanders present during the imaging, in particular, during motion of the gantry (eg, C-arm of a C-arm X-ray imaging apparatus).

According to one embodiment, the apparatus comprises an action module configured to issue an output signal for an object approach action to be taken if the response signal or the filtered response signal fulfils a second condition, in particular crosses a second threshold as measured relative to said new base value.

The object approach action includes in particular, but not necessarily in all embodiments, an object collision avoidance action, such as a slowing down or a change of trajectory of the relevant moving part associated with a motion of the sensor, before a touch event occurs. Object approach action may also include a mitigation action such as halting the relevant moving part after a touch event occurred.

According to one embodiment, said response signal is received whilst there is relative motion between the at least one proximity sensor and at least one object. In one embodiment, it is the proximity sensor that is moving due to it being mounted on a movable part, such as the C-arm or other.

According to one embodiment, the filter module is configured to reduce those one or more frequencies in the response signal that are due to the at least one proximity sensor and the (one or more) object passing each other in relative motion. For instance, the filtered out frequencies are those that one observes when the proximity sensor is moving through space and in doing so moves past object(s) in the surrounding. Alternatively, the proximity sensor is fixed and it is the object(s) that are moving past the sensor.

According to one embodiment, the filter module is high-pass or band-pass.

According to one embodiment, the proximity event declarator is configured to monitor said filtered response signal or the unfiltered response signal and to re-declare the proximity event into a non-proximity event if the filtered response or the unfiltered signal crosses the first threshold again and wherein the action module is configured to issue said output signal only if the proximity event is declared. By "unfiltered" is meant, that the above mentioned filtering module has not been applied. Other possible signal conditioning may or may not have been applied.

According to one embodiment, the at least one proximity sensor is mounted on a movable part of a work equipment, in particular, of a medical work equipment, yet more particular, of a medical imaging apparatus.

According to one embodiment, the proximity sensor is integrated into a wearable for attachment to the human body.

According to one embodiment, the responses are capacitance readings.

According to a second aspect of the invention, there is provided an imaging system comprising:
 an imaging apparatus;
 an object approach detection apparatus as per of any one of the above mentioned embodiment; and
 one or more of the proximity sensors from which the response signals are received.

According to one embodiment of the system, the at least one of the proximity sensors is arranged on i) a movable part of the imaging apparatus and/or wherein the at least one proximity sensor is arranged ii) on the body of a human residing in a surrounding of the imaging apparatus.

According to a third aspect of the invention, there is provided a method of object approach detection, comprising the steps of:
 receiving a response signal from at least one proximity sensor measured relative to a first base-value of said at least one sensor;
 filtering said response signal to produce a filtered response signal;
 declaring a proximity event has occurred if the filtered response signal fulfils a first condition, in particular crosses a first threshold,
 choosing a new base value in response of the declaring that the proximity event has occurred.

According to one embodiment, the method comprises:
 issuing an output signal for an object approach action to be taken if the response signal or the filtered sensor signal fulfils a first condition, in particular crosses a second threshold as measured relative to said new base value.

In sum, the proposed apparatus and related method allows securing the following advantages:
 Reduced collision risk because occurrence of "false positive" situations can be reduced.
 No continuous monitoring of the base-value is required, thus reducing computational expense and/or failure modes.
 No base-value history required at system power-up.
 No manual intervention required for system calibration (which may be time consuming). Calibration allows ensuring the sensor(s) are "accustomed" to their surroundings which include physical objects around them and environmental factors like temperature, humidity, etc. Non-calibrated systems are in general prone to under or oversensitivity as well as to false detections.
 Ability to differentiate between non-contact proximity and physical touch. This is at least in part because of the frequency suppression used herein. Specifically, the filtered signal has been found to be particularly sensitive to object approach events that involve a human or animal body part. Typically as a part of the human body approaches the sensor or is being approached by the sensor, the filtered signal starts rising exponentially. At the occurrence of a touch event the rise in the filtered signal is especially steep. Just like it is possible to set a first threshold that detects a proximity event, it is also possible to set a second threshold (higher, than the first threshold). This second threshold allows detecting said steep rise in the (filtered or unfiltered) signal caused by a touch event as opposed to a mere proximity event as per the first threshold.
 Improved robustness against environmental conditions (humidity, temperature) on system performance because base value is being adapted.

BRIEF DESCRIPTION OF THE DRAWINGS

Exemplary embodiments of the invention will now be described with reference to the following drawings (which are not necessarily to scale) wherein.

DETAILED DESCRIPTION OF EMBODIMENTS

Figure 1:
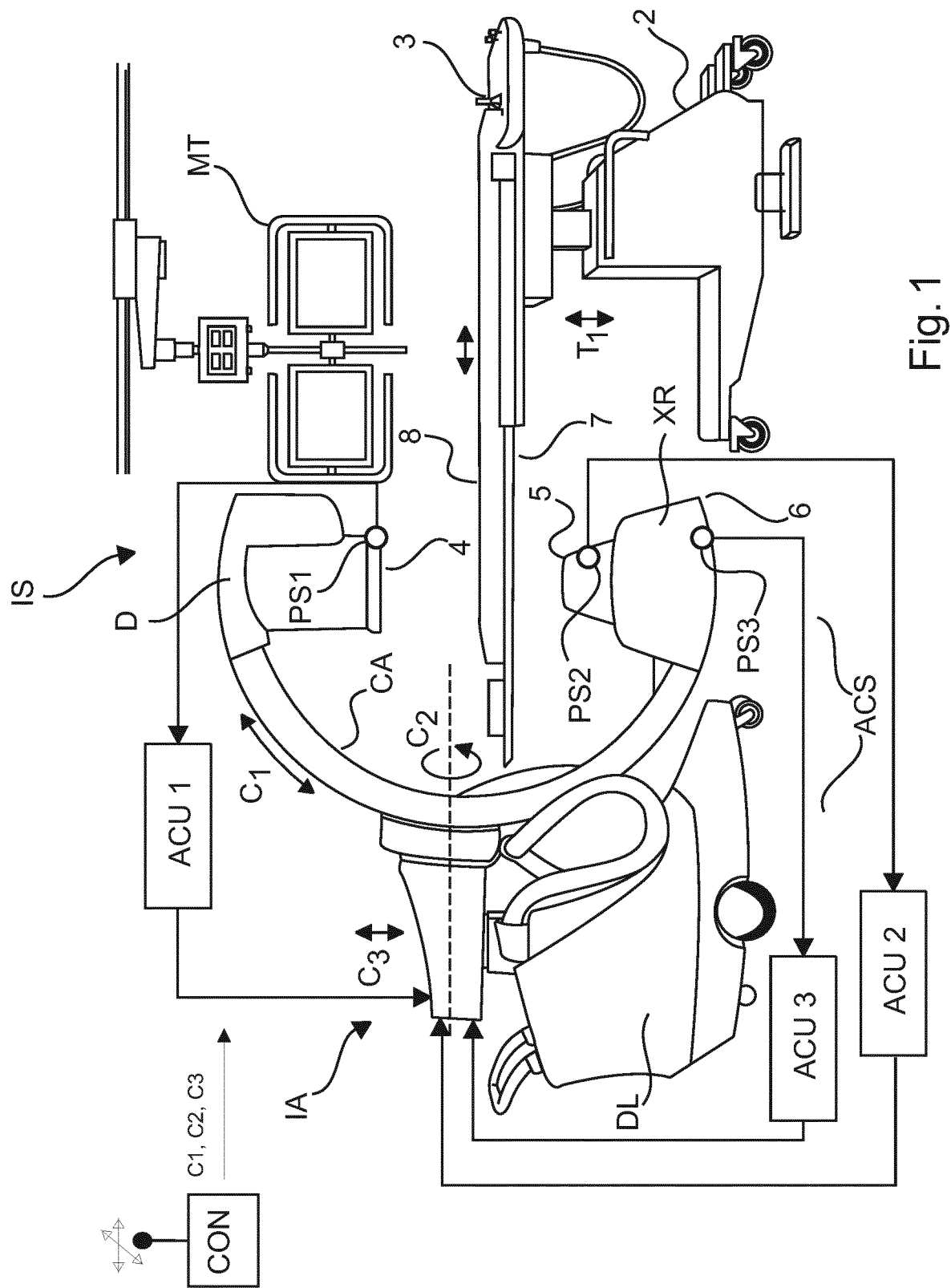
FIG. 1 shows an imaging arrangement including an object approach detection (sub-)system.

With reference to FIG. 1 there is shown a work equipment arrangement with one or more movable parts. In particular and as envisaged in one embodiment, FIG. 1 shows schematically an imaging arrangement IS, comprising an imaging apparatus IA and an object approach detection system ACS.

The imaging apparatus is in particular but not necessarily in all embodiments an X-ray imaging apparatus. It comprises imaging components, in particular an X-ray source unit XR (also referred to herein as "the XR source") and an X-ray sensitive detector unit D (also referred to herein as "the detector") arranged to detect radiation emitted by the source XR. The X-ray unit XR comprises an X-ray tube which is housed inside a source housing. The detector unit D comprises an X-ray radiation sensitive surface such as that of a flat panel detector or similar and associated electronics to capturing an X-ray image. The detector electronics and the X-ray radiation surface is likewise housed in a detector housing.

There is a patient table 2 with a table top 7 and for patient comfort optionally a mattress 8. The patient table is positionable in an imaging region between the X-ray source XR and the detector D. The table may be height adjustable along T1 other manually or via suitable actuators. The imaging apparatus, in particular the X-ray imaging apparatus is primarily envisaged for medical purposes but other applications not medical are not excluded herein. In other words, although in the following we may mainly refer to a medical context, this does not exclude other contexts. In the type of medical X-ray context mainly envisaged herein, the patient is positioned on the table top.

The X-ray source unit XR and detector unit D are arranged on a gantry CA. In the embodiment shown the X-ray imager is of the C-arm type but again this is not limiting as other imager constructions are also envisaged herein. As the name suggests the gantry, the C-arm imager, has a letter "C" or (overturned letter "U") shape, at one end of which there is attached the X-ray source unit and at the other, opposite end, the detector unit D.

The C-arm is moveably arranged in a cradle structure. The cradle structure which may be stationary fixedly mounted to the floor or the ceiling of the examination room or it may be a mobile solution as shown in FIG. 1 where the cradle is integrated into a moveable dolly DL so that the X-ray imaging apparatus IA can be moved about from room to room.

The C-arm structure forms a movable part of the imaging apparatus. The C-arm is formed of a material of sufficient stiffness such as a metal or other, to be able to safely carry the weight of the imaging components with practically no or very little deformation, even during motion of the arm CA.

In particular, the C-arm can be rotated about one or more axis around the imaging region. For instance one rotation axis which runs parallel to the drawing plane in FIG. 1, is indicated as $C_2$, another rotation axis runs perpendicular into the drawing plane of FIG. 1 and the corresponding rotations are indicated by $C_1$. In addition or instead, the C-arm structure CA may also be height adjustable relative to ground. This is shown as $C_3$. In addition or instead of rotational movement, the C-arm CA may also be translatable. The one rotation(s) or translation(s) are enabled by suitable mechanics in the cradle.

The motion of the C-arm confers a corresponding motion to the detector D and X-ray source XR. The presence of the C-arm gantry CA is not envisaged in all embodiments however. Alternatively to C-arm induced motion of the imaging components, these may be instead wall, floor or ceiling mounted on suitable guiderail(s) and/or on telescopic/articulated arm(s), etc. In particular in these embodiments, the imaging apparatus may be arranged to allow motion relative to the imaging region of the imaging components individually and independently from each other.

The movability of the C-arm and/or that of the X-ray source and the detector D allows acquiring, preferably real-time, X-ray imagery from a number of different angles or projection directions. This is of great value for instance for diagnostic or interventional purposes. For instance, in the later application a catheter or a similar medical device must be navigated inside the patient's body. It is therefore of premium value that the interventional radiologist is informed precisely where within the human body the medical device resides at all times.

In one embodiment, the motion (along or around the one more axis) of the C-arm CA is effected manually by the user via a hand-wheel mechanism or similar. Preferably however, there are arranged instead suitable actuators like servo or stepper motors which are electronically controlled by the user. For instance, in one embodiment the motion of the C-arm and hence that of the X-ray source and/or detector can be controlled by an operator panel or console CON. The operator panel may comprise a suitable button operating equipment such as a joy stick, etc., which allows for intuitive spatial control of the C-arm position. There may also be a corresponding panel 3 for table height adjustment. Instead of user control, fully-automatic motion control is also envisaged. For instance, the precise motion may be requested by a protocol in which the motion commands are issued by a protocol interpreter arrangement such as a processor that processes a set of instructions in which the protocol is encoded. The processor may be realized as a general purpose computing unit suitably interfaced to the actuators of the imager IA. In one embodiment the imaging apparatus is equipped with both manual and actuator control so the user can choose how to effect the desired motion of the imaging components.

Without limiting the above or the following, reference is now made in more detail to the C-arm embodiment. In use, the C-arm rotates around one or two or more rotation axes into the suitable imaging position relative to the imaging region, or more specifically, relative to the anatomy of interest. Instead, or in addition to rotation, the C-arm may also be translated and tilted depending on the specific degrees of freedom allowed by the specific model. Once moved (that is rotated and/or translated, etc.) into the desired position relative to the patient anatomy of interest, the user or protocol interpreter issues an image acquisition command. Once this is issued, X-ray radiation is emitted from the X-ray source XR, exits the X-source via an egress window and then passes through the patient. The emitted X-ray radiation interacts with patient tissue and the radiation after interaction emerges from the far end of the patient and is then registered at the detector D. More specifically, the emerging radiation passes through an ingress window of the detector unit D and then impinges on a radiation sensitive surface or the detector unit D. The impinging radiation causes electrical signals which are processed by suitable signal processing circuitry into one or more images which can be visualized on one or more monitors MT. The X-ray images so generated can then be used by medical personnel to study the internal configuration of the patient, for instance organ structures, their boundaries and/or the position of a catheter inside the patient. Although reference is made herein to X-ray imaging, other modalities such as phase contrast imaging, ultrasound or others are also envisaged herein instead of or in addition to X-ray.

The C (or U-arm structure) of the C-arm is in general formed from a material of sufficient stiffness (such as metal core). This allows stably arranging the X-ray unit and the detector unit opposite each other to form an imaging examination region around which the X-ray source and the detector can rotate.

As will be appreciated from the construction and the functioning of the imaging apparatus IS, the moveable part or parts, in particular the C-arm, may inadvertently hit or collide with equipment or personnel situated around the patient. The rigidity of the C-arm, combined with the relatively high speed with which it rotates, can cause considerable damage or injury when a collision with equipment or humans occurs. This relatively high speed of rotation is sometimes necessary because the X-ray imaging apparatus IA is used for instance in an emergency situation such as in emergency (A&E) units where it is essential to quickly acquire images along different viewing directions to ensure patient safety such as in emergency operations etc. Even the patient lying on the table top is not necessarily safe from being hit by the moving C-arm. For instance, inadvertently raising their head or sliding their arm outside the table top may cause injury. Another reason for the requirement of relatively high rotation speed is the desire to perform 3D imaging where projection images from different angles around the patient are acquired and these are then reconstructed by suitable image processor into 3D images of the inner anatomy of a region of interest of the patient.

To prevent such collision events from happening, or at least reducing the risk for those to happen, the imaging system IS includes an object approach detection system ACS such as an anti-collision system (likewise referenced herein with reference character "ACS").

Figure 2:
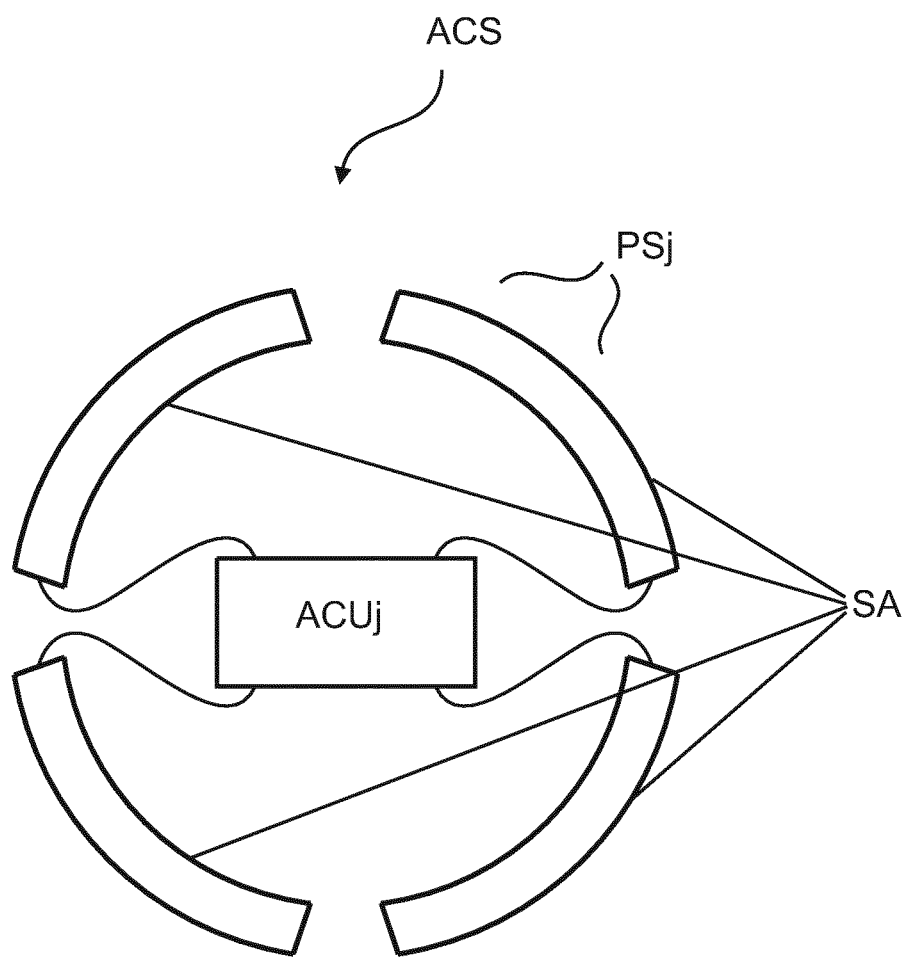
FIG. 2 shows a close-up of the object approach detection system as used in FIG. 1.

Components of the anti-collision system ACS are shown in a block diagram of FIG. 2.

The anti-collision system ACS comprises one or more proximity sensors PS and one or more anti-collision units $ACU_j$.

A proximity sensor PS is broadly made up of one or more sensing areas SA. In the exemplary embodiment in FIG. 2, four sensing areas SA are shown but a single, two, three or more than four sensing areas are also envisaged. Broadly, the proximity sensor is capable of detecting an object approaching the sensing area. Upon approach, the response signal is issued by the proximity sensor and this response signal is then interpreted by at least one of the anti-collision units $ACU_j$. The anti-collision unit processes the one or more response signals and produces, when certain approach conditions are met, an output signal which can be used to effect a suitable object approach action. This action may include for instance, holding or slow down the motion of a respective one or more sensors $PS_j$, associated with a relevant moving part, such as of the C-arm CA.

Referring back to FIG. 1, the one or more proximity sensors (as an example three sensors are shown in FIG. 1, labelled $PS_1$-$PS_3$) are associated with the respective moving part by suitable placement. Specifically and preferably, the one or more sensors $PS_j$ are arranged at notorious collision zones of the imaging apparatus IA. For instance the proximity sensor may be arranged at the housing the detector unit D. More specifically, a proximity sensor, referenced as $PS_1$ in FIG. 1, may be arranged at or around the radiation ingress window 4 of the housing where the radiation passes through and onto the radiation sensitive surface. In other words, proximity sensor $PS_1$ may be arranged on that part of the detector unit D housing that is proximal to the X-ray unit XR. An arrangement at the detector housing at a distal part, in particular at an edge thereof, is also envisaged (not shown).

In addition thereto or instead to proximity sensor arrangements at the X-ray unit XR, a proximity sensor $PS_2$, may be arranged at the X-ray source XR. More particularly, a proximity sensor $PS_2$ may be arranged at radiation egress window 5 of the X-ray unit housing. In addition or instead, a proximity sensor PS3 may be arranged at am edge 6 of the X-ray tube housing distal from the egress window 5. In one embodiment the one or more proximity sensors PS1-PS3 are arranged to the inside of the respective housings of the X-ray unit or the detector unit. However, arrangements on the outside of the housings, or in general on external surfaces of the imaging apparatus IA, are also envisaged in some embodiments. In fact, any suitable placement of the one or more proximity sensors $PS_j$ on moveable parts of the imaging apparatus is envisaged. For instance, the one or more proximity sensors $PS_j$ may also be placed on one or more locations on the C-arm itself. It may be preferable however to arrange, as shown in FIG. 1, the proximity sensors at certain extremal or exposed locations of the moving part(s) that can be expected to be more prone to attract collision.

As mentioned earlier, it is also the patient table which may be height adjustable $T_1$ by operation of suitable actuators. It may therefore also be opportune in some scenarios to arrange proximity sensors at the motorized patient table. However, the motion performed by the patient table in the up and down or even horizontal motion is relatively slow compared to the relatively quick motion of the C-arm. It is more preferable to arrange the proximity sensors on those parts that move relatively quickly compared to others. The placement of the proximity sensors have been explained with particular reference to FIG. 1 which shows a C-arm imaging apparatus. In other medical settings or non-medical settings, for instance in industrial settings, where moving parts are those of an industrial robot, other placements on autonomous or semi-autonomous, or remote controlled equipment with moving parts are of course also envisaged.

With continued reference to FIG. 2 and as mentioned earlier, each proximity sensor $PS_j$ may include more than one sensing area SA. Using more than one sensing areas, such as four as exemplary shown in FIG. 2, allows not only detecting the presence of an approaching object, but also allows localization in 3D. If a plurality of proximity sensors are used it is not necessary that each proximity sensor has the same number of sensing areas. For instance, at some locations in the imaging system, sensors with a single sensing area may be sufficient whilst in others two, three or more than four sensing areas are required because more details about the object approaching at the relevant location are required. In other words, in one embodiment each position sensor comprises of only a single sensing area whereas in other embodiments each proximity sensor comprises a plurality—two, three or more sensing areas, but mixed embodiments are also envisaged where some proximity sensors comprise only a single and others a plurality of respective sensing areas.

The preferred type of sensor envisaged herein is of the capacitive type, as they have shown to produce reliable results that work well in medical imaging contexts, are relatively low cost, have low power requirements and have high reliability. Certain other types of sensors are not excluded herein and include: inductive, magnetic, infrared, thermal, Hall effect-based, optical or sonic-based (in particular, ultrasonics-based), etc. These types of proximity sensors are distinguishable by the physical quantity onto which the object approach is modulated upon.

The proximity sensor setup, as proposed herein, is mainly envisaged as non-contact based sensing (the capacitance sensors being the preferred embodiment) in distinction to contact-based sensing. However, as will be explained further below, the ACU envisaged herein can be configured so that the non-contact sensors can be used as contact-based sensors.

Turning now in more detail to capacitive proximity sensors according to one embodiment, in these, each sensing area SA essentially comprises a pair of electrodes such as metallic plates suitably positioned from each other at a distance to form a capacitor. In capacitive type proximity sensors the dielectric property of an approaching object disturbs the capacitance of an electrical field which is built up between the electrodes of the respective sensing area, it is this change in capacitance that induces a voltage or current change which can be captured by suitable electronics and interpreted as a tell-tale for how far the object is from one or both of the electrodes.

As an alternative, the sensing area for each sensor may be formed from a single plate whilst the role of the other electrode is taken up by the approaching object. These type of sensors with "single plate" sensing areas are the preferred embodiment herein but that is not to exclude arrangements that use the above described embodiments with pair-wise electrode plates. The single plate sensing area can be arranged in one embodiment as a conductive pad laid out in a PCB or on glass.

In either of these sensor embodiments, in case there is no object present within a certain vicinity of the (respective) sensing area, the capacitance will assume a certain stable base-value (also referred to herein simply as "baseline" or "baseline-value"). This baseline value may change because of changes in ambient conditions such as temperature, humidity etc. The base line value may need to be established initially upon power up of the object approach system ACU in a calibration phase. The proximity sensor response signal essentially measures or corresponds to the amount by which a detected capacitance deviates from the base line capacitance. This concept of baseline-value is also applicable to detector types other than capacitive (as mentioned above), so the following is of equal application to these alternative detector types although capacitive sensor remain, as mentioned, the preferred embodiment and the following is described with main reference to capacitive type sensors.

As will be explained in more detail below, some known systems operate a "simple" thresh-holding in which an anti-collision action will already be taken as soon as this deviation exceeds a certain threshold given a fixed baseline value. As will be explained in more detail below, the proposed system is unlike this because the proposed ACU system uses a dynamic thresholding scheme. In this dynamic thresholding scheme, the baseline varies in a specific way and whether or not an action is taken does not only depend on a specific baseline deviation but also on the magnitude of the baseline itself, that is, whether the ACS is in an excited or proximity state.

Specifically, the proposed system operates a dynamic thresh-holding where the base line is continuous monitored and adapted and collision evasive action is taken only if the anti-collision system is in the excited or proximity (event) state. In more detail, the anti-collision unit ACU as proposed herein is a signal processor configured to resolve signal responses received from the proximity sensor(s) into i) proximity events based on frequency suppression and ii) persistence of these events. Detection of proximity persistence is achieved in one embodiment by essentially instantaneous base value capture ("single-point base value capture") at the instance of proximity event occurrence at a sensing area. It is this base value so captured that is then used for monitoring the response signals at the sensing area(s). The processor ACU is capable to differentiate between non-contact proximity and physical touch, provided that a sufficient time interval exists between an object causing a proximity event and the actual touch event. The processor is capable of detecting proximity events and thereby enabling the system to be consistently stopped at a specified distance less than or equal to 40 mm, the said distance being adjustable via configurable software parameters (eg, parameters $T_c$ and/or $T_p$, for which see below at FIG. 6 where these parameters are discussed). Preferably the signal processing is in real-time.

Figure 3:
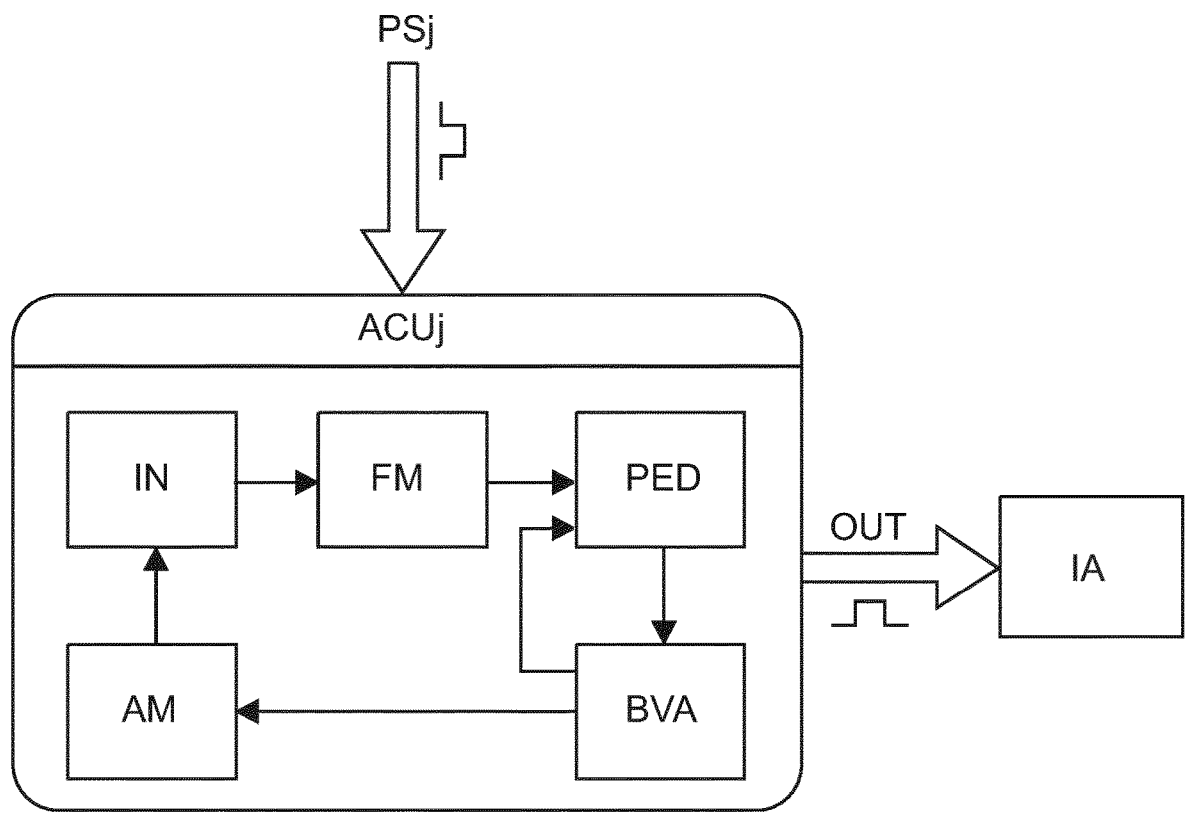
FIG. 3 shows in more detail a processing component of the object approach detection system of FIG. 2.

FIG. 3 shows in more detail a block diagram of components of an anti-collision unit $ACU_j$ as envisaged herein in one embodiment. There is an input port IN with suitable data acquisition circuitry (not shown) that is capable of receiving response signals from the one or more proximity sensors $PS_j$ and the so received signals are processed into digital form by an A/D (analog-to-digital) conversion stage. The data acquisition circuitry may also include some signal conditioning circuitry, such as an amplification component, etc. According to one embodiment the data acquisition stage includes in one embodiment applying a predefined current into the capacitor plate at a high frequency square pulse. This turns the sensor into a switched capacitor. From the voltage drop across the switched capacitor the equivalent resistance and thus the capacitance of the sensor can be measured. An internal A/D convertor converts this calculation to a digital value to form a proximity response signal, ready to be processed.

The so digitalized proximity response signal is then processed in a filter module stage FM to suppress or even eliminate pre-defined frequencies in the response signal. More particularly, response variations that are due to a mere motion of the proximity sensor relative to its surroundings are being suppressed. As will be appreciated from the setup in FIG. 1, whilst the C-arm CA is moving, the proximity sensor(s) $PS_j$ attached thereto will trace out a trajectory in space and while doing so will pass by surrounding objects, such as equipment, persons (medical personnel or bystanders), etc. without collision. These harmless, repeated approaches to objects in the surrounding will however induce fluctuations of the respective baseline values of the proximity sensors. The filter module FM is configured to desensitize the sensor to those harmless approach events. It is to be noted herein that the "raw" sensor signals x, that is, the ones provided by the data acquisition stage prior to filtering by filter module FM, are retained herein (in a buffer storage or similar) as they will be further processed at later stages alongside the filtered signal which will be soon apparent below.

Referring now back to the filtered signal y, this is monitored at proximity event declarator stage PED against a first threshold. If the filtered signal y fulfills a first condition in relation to this threshold, e.g., the filtered signal crosses the threshold (that is, exceeds or falls below said threshold), the proximity event is declared for a given sensor or a group of sensors. The occurrence of this event can be lodged by setting a flag in a suitable data structure that allows associating sensor identity and proximity event. In case only a single proximity sensor is used this can be implemented as simply setting a binary variable='1' or ='0' to lodge whether or not the proximity event has occurred. If a plurality of sensors is used, a tabular data structure may be used to lodge the sensor identity dependent proximity events.

When the proximity event occurs, a base value adaptor stage BVA becomes active to set a new base value to replace a current base line value which was set at an earlier phase, for instance upon power up of the system ACS or it was set manually by the user. The new baseline value is computed from the unfiltered raw signal x as received before or preferably after the proximity event has been declared.

The instant at which occurrence of the proximity event is declared marks the beginning of the proximity period. After the proximity event has been declared for a sensor $PS_j$, the BVA preferably constantly monitors the filtered sensor response signals for whether the declaration of proximity period/event can be upheld or whether the proximity event is still in effect. In this way it is ascertained whether the filter sensor response violates the first condition, e.g., whether signal y crosses the first threshold again. If this does not happen, the proximity event state is maintained. Otherwise the proximity reverts to a non-proximity state and the PED operates to so re-declare by resetting the relevant flag. In other words, the anti-collision unit processor ACU is configured to monitor the persistence of the proximity event.

Whilst the proximity event is in effect, an action module AM can operate to issue a request as an output signal at output port OUT for an object approach action (such as a collision avoidance action) to be taken. The output signal (also referred to herein as the "action signal") is issued if the unfiltered response signal or the filtered response signal received within the proximity event period deviates by more than a pre-defined second threshold from the newly defined base line value. If such a deviation is detected, and the proximity event is still in effect, only then the request for the action signal is issued at output port OUT.

The output signal is then intercepted by actuator control circuitry of the imaging apparatus. By suitable drivers and interfaces the collision avoidance action is then effected. The collision avoidance action includes actions such as slowing down, stopping or otherwise acting on the respective moving part of the imaging apparatus at which the respective proximity sensor is mounted.

Figure 4:
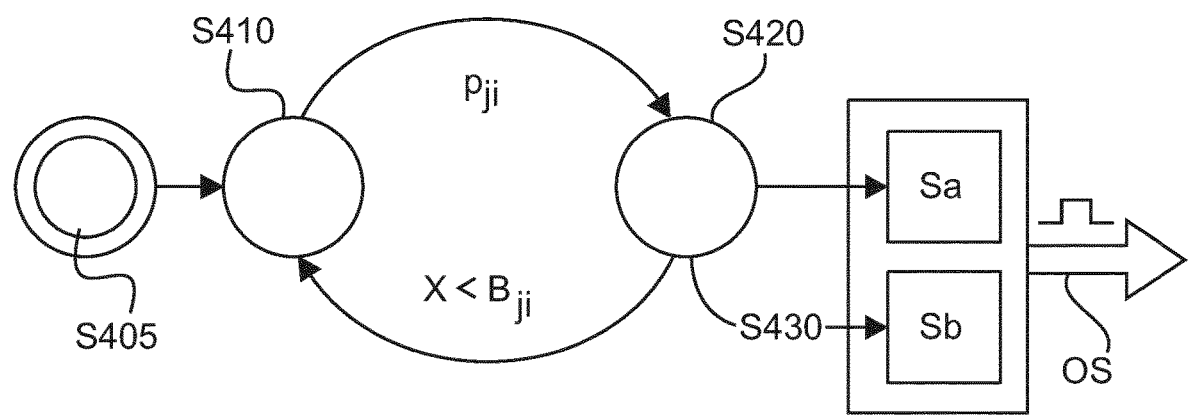
FIG. 4 shows a state diagram of the processing component as per FIG. 3.

As summarized in the state diagram of FIG. 4, the anti-collision unit ACU as proposed herein is capable of operating in two states, in an active state or an inactive state which may be called the "proximity state" and a "non-proximity" state. The detection of the proximity event marks the instant when the non-proximity event is abandoned for the proximity state.

At an initial state S405, such as at system power up etc. or user adjusted, a certain default baseline value is set for a given sensor PSj. All sensors, should there be more than one, can be given the same baseline value or different baseline values. In one embodiment, the last available baseline value(s) for the PSj may be stored at power-off and this/these is/are then reused at power-up. The system then enters idle mode or the non-proximity at stage S410. If a proximity event $p_{ij}$ is detected, the system enters the second, excited state, namely the proximity state at S420.

The system remains in proximity state by monitoring the filtered sensor signal. If the filtered input signal violates a predefined first condition, e.g. drops below the first threshold $B_{ij}$, the system returns to the non-proximity state or idle state at S410. The notion "$B_{ij}$" means that the first threshold is for the j-th sensor and this threshold is the i-th one that has been set for sensor j. A similar notion has been used above for the proximity event denoted as $p_{ij}$.

When in the proximity state S420, the newly acquired base line value is used against a second threshold. In other words, in state S420, deviations of the filtered or unfiltered signal are now measured against this new baseline value. If this second threshold, whilst in excited object proximity state, is crossed (that is, if the filtered or unfiltered signal exceeds or drops below the second threshold) then a non-contact proximity action signal Sa can be issued and output as output signal OS. Alternatively, in this excited state, the system can monitor with a second threshold suitably chosen for a touch signal event S430 and only then will the action signal Sb output as output signal OS. That is, whilst in the proximity state, the anti-collision unit can be configured to operate for contact or non-contact based sensing: based on the new baseline value and monitoring against the second threshold, the action signal is already issued when the approaching object is sufficiently close to the sensing area or if the object actually touches the sensing areas, depending on how the second threshold is set.

Depending on the filtered or unfiltered sensor response signal, the anti-collision unit ACU as proposed herein oscillates between the two states, non-proximity and proximity, and takes action only when the system is in the proximity event and when the second threshold is crossed. In this way the system is desensitized against, preferably low frequency, baseline value fluctuations caused solely by relative motion between the proximity sensor and the surrounding objects. These surrounding objects are sufficiently close to elicit an appreciable sensor response but are nevertheless outside the trajectory of the proximity sensor as it traces out its path during the motion of the respective moving part CA. Occurrence of false-positive or false-negative situations can be minimized with the proposed two-state approach.

The anti-collision unit ACU as proposed in FIGS. 3 and 4 can be implemented purely in software but preferably is implemented in hardware as dedicated integrated circuits (IC). The data acquisition stage IN is preferably integrated with the remaining components as shown in FIG. 3 but this may not necessarily be so in all embodiments. For instance, the data acquisition stage IN may be outsourced to the sensor locations themselves and the response signals are then communicated to the remaining components of the ACU in a wired or wireless manner. An embodiment where the ACU components are all fully integrated may be implemented in a suitable SOC (system-on-chip) which has been observed to yield good results. Depending on the complexity of the filtered computations, for instance on the order of the filter etc., memory and CPU requirements may be modest and the method has been found by Applicant to be implementable in relatively cost effective SOCs. For instance a specification of an 8-bit microcontroller, with 16 KB flash memory (including memory required for storing the code) and 1 KB RAM has been shown to suffice in some circumstances. The IC can be arranged as a suitably programmable FPGA (field-programmable-gate-array) or as a hardwired IC chip. As an alternative to the IC setup, the components of the ACU can be arranged on PCBs (printed-circuit board) with a microcontroller.

As further shown in FIG. 3 in view of FIG. 1, each proximity sensor may have its dedicated anti-collision unit $ACU_j$ to which it is interfaced. However, this may not necessarily be so in all embodiments. For instance in an alternative embodiment, a single, centralized ACU is used which processes the response signals from all the proximity sensors.

Other than purely IC based arrangements are also envisaged where only the data acquisition stages are performed locally whilst the remaining functionalities of the ACU are performed centrally on a general computing unit that receives the digitalized signals ICs.

In any of the above described arrangements, the one or more ACUs are suitably interfaced to the one or more proximity sensors arranged at the imaging apparatus. The sensor response signals can be forwarded by wired or wireless communication to the one or more anti-collision units ACU.

Figure 6:
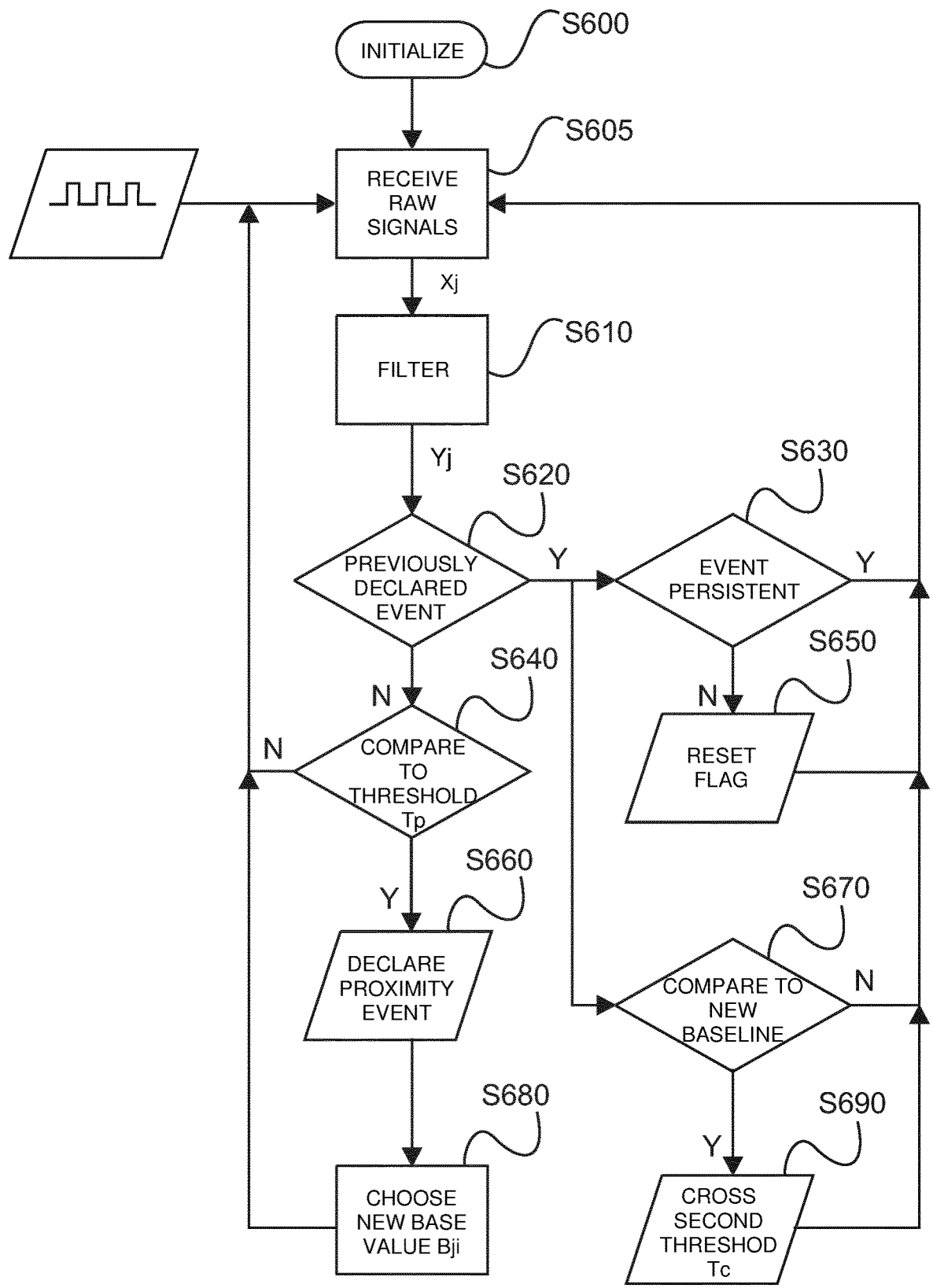
FIG. 6 shows a flow chart of an object approach detection method.

Reference is now made to the flow chart in FIG. 6 where a method for object approach detection is explained in more detail. It should be noted that the method steps to be described below are not necessarily tied to the architecture described above in FIGS. 1-4 and the description of the method below may also be understood as a teaching in its own right.

At initialization step S600 the object approach detection system, such as the anti-collision unit explained earlier, is powered up and an initial base line value for one or more proximity sensors is generated. The initial base line value may also be user supplied.

Against this initial base line value, (raw) response signals are received from one or more proximity sensors at step S605. These (raw) response signals will be referred to herein with lower case letter x such as $x_J$ for a signal received from sensing area J of a sensor. Preferably the proximity sensors are of the capacitive type but other technologies are not excluded herein as long as they apply the previously explained concept of base line measurements against which the readings received from an approaching object are measured.

As mentioned earlier in relation to FIGS. 1,2, one or more of the proximity sensors are attached to one or more movable parts of a work equipment, such as an imaging system, in particular a medical imaging system, yet more particular, a C-arm system. The received response signals are preferably digitized by A/D conversion. In one exemplary embodiment, the response signal (e.g., sensor capacitance values) is provided in the form of digital input at 16-bit resolution, preferably at a fixed sampling rate. The resolution can also be higher or lower depending on the available hardware, but should preferably be provided with a minimum of 12-bit. The raw response signal received from the sensor(s) should be linearly related to the capacitance of the sensor. Also preferably, the approximate stable capacitance baseline value $X_s$ of all the sensors should be half of the chosen signal resolution. Preferably, for each sensing area, the capacitance values are processed separately herein as per the following steps. The response signal $x_J$ as received at step S605 is generally provided whilst there is relative movement between the sensor and objects in the surroundings of said proximity sensor. The term "object(s)", as used herein, includes inanimate objects such as equipment, etc. but also includes humans or animals that at least partly reside in the vicinity of the working equipment during motion of the moveable parts to which the proximity sensor is attached. The response signals so received up to this point are those measured as deviations against the initial base line value.

At step S610, a filtered signal $y_J$ is computed from the raw data stream $x_J$ as received from the sensors. More particularly at step S610 the acquired raw sensor response signal for each sensor is passed through a frequency suppression filter but the original, raw, signal x is still retained. It will be understood then that the qualifier "raw" refers to a sensor signal to which this filtering step S610 has not been applied.

The filter is preferably a pre-computed digital IIR filter, in particular a Butterworth bandpass filter. A difference equation of the filter is according to one embodiment:

$$y_j[n] = 0.561 x_j[n] - 0.561 x_j[n-2] + 0.812 y_j[n-1] + 0.122 y_j[n-2] \quad (1)$$

where, $j = 1, 2, 3, \ldots, K$, and K is an index for respective sensing area of the sensor(s) $PS_j$ and n is the sample instance. The filtered signals $y_j$ are essentially desensitized against low frequency variations in the sensor response signals $x_j$, which are generally caused by (relative) sensor movement. Therefore, movement of the sensor in the absence of any proximal object, causes no or very little excitation in the filtered signals. Although the coefficients in (1) of about (0.6, 0.6, 0.8, 0.1) are envisaged in one embodiment, this is not limiting, as other coefficients may also be used.

Figure 5:
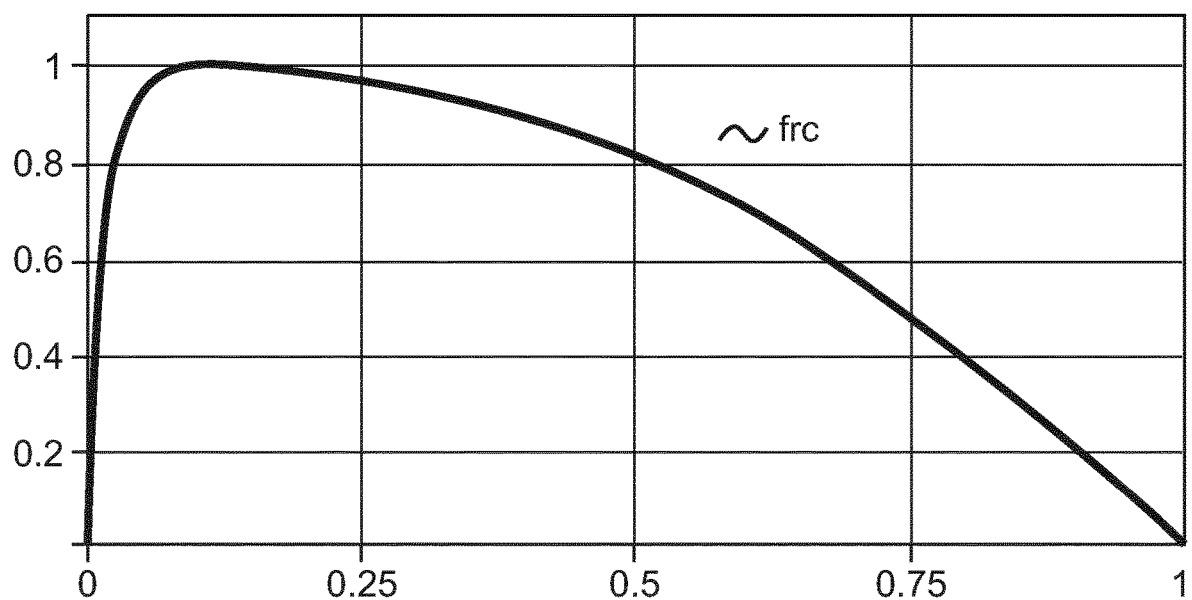
FIG. 5 shows a frequency response curve according to a filter module as used in the processing component as per FIGS. 3 and 4.

An exemplary frequency response curve frc of the frequency suppression filter is shown in FIG. 5. The frequency response curve frc is graphed in FIG. 5 as normalized frequency versus gain. Specifically, gain is graphed vertically and the normalized frequency is graphed horizontally. Normalized frequency is expressed in normalized units of half-cycles per sample (or equivalently, cycles per "2 samples"). In normalized frequency representation in half-cycles, the frequencies are normalized by the Nyquist frequency (that is, twice the sampling rate). Other, equivalent, in particular normalized, representations are also envisaged herein, such as cycles per samples, where normalization is by the sampling rate.

The frequency response curve frc has characteristics of a band-pass filter with normalized frequency band between about 0.05 and 0.75. A high pass filter may be used instead, as it has been found that it is in particular low frequency components that are related to relative movement of the sensor versus the surrounding, and we wish to eliminate essentially these low frequency components. It was a surprising finding that filters with anfrc having a "shark-fin" like profile similar to that in FIG. 5, work in a number of different settings irrespective of the specific configuration of the surroundings in which the sensor is moving. By "low" we mainly envisage normalized frequency components below 0.01 or below 0.02 or below 0.05 but this is according to one embodiment only and is not necessarily to limit the system as described herein.

More specifically, to estimate the frequency band of interest, a time-frequency analysis of prior test sensor data can be performed using a Continuous Wavelet Transform (CWT). Comparing the CWTs of various logged training sensor signals, the normalized digital frequency band of interest was chosen to be 0.018 to 0.595, or about 0.02 to 0.6 or about 0.05 to 0.75 as mentioned above. A first order IIR Butterworth bandpass filter was constructed for these bands with the difference equation as per (1). As shown in the exemplary embodiment of FIG. 5, the frc has a relatively steep slope up to the lower end of the frequency band and then tappers off with relatively lower downward slopes increasing towards the higher end of the frequency band. Higher order filters would no doubt give a more band conforming frequency response function. However, the order has been limited due to the computational constraints imposed by floating point calculations in the microcontroller used on the ACU. An advantage of using a first order filter is that there a time delay can be reduced when computing the filtered signal.

At step S620 it is established whether a proximity event has already been declared for the relevant sensor or group of sensors and whether this event is still in effect. This can be established by examining a status (yes/no) of a related flag as lodged into a suitable record as has been explained above in relation to state diagram FIG. 4.

If no proximity event is currently in effect, method flow proceeds to step S640 where the one or more filtered detector response streams are compared against a pre-set threshold $T_P$. For a plurality of sensor response signals $y_j$ (sensed by a plurality of sensors $PS_j$), a first condition or criteria for a proximity event to occur at a given sensor $PS_J$ can be formulated as follows:

i.a) $y_J > T_P$ or i.b) $y_J + y_{J+1} > T_P$ or i.c) $y_J + y_{J-1} > T_P$ ii) $y_J \geq y_j \forall j \neq J$ where sensing areas J−1, J and J+1 are physically adjacent to each other (note that if J=1, J−1=K; and if J=K, J+1=1).

It will be appreciated in the event that there is only a single proximity sensor it is only condition i.a.) that is considered, that is, a proximity event is declared if the filtered signal from the proximity sensor crosses, for instance, exceeds the threshold $T_P$.

More particularly, until a proximity event does not occur, the filtered signals are only observed and no action is taken. If at any point in time, an excitation larger in magnitude than $T_P$ (for example, $T_P$ can be 1.3% of $X_s$) is observed in any of the individual filtered signals $y_j$ or a combination of adjacent signals, a proximity event is declared to have occurred at the sensor J.

According to one embodiment, the above conditions i.a-i.c) and ii) need to be satisfied in order for a proximity event to be declared at the sensing area J.

The relations i),ii can also be used in isolation and to arrive at a number of different embodiments. For instance in one embodiment it is only condition ii) that is considered, that is, only the signal from the most dominant filtered response signal is considered against the first threshold $T_P$. Further, in the event of a group of cyclically arranged proximity sensors, it is not (only) the individual proximity response that is measured against the threshold TP but it is the (possibly weighted) sum of neighboring proximity sensors (schematically indicted as J−1 or J+1) that are also or instead considered as expressed in conditions i.b), i.c).

If the conditions interrogated for at step S640 are met, a proximity event is declared to have occurred step S660 and this is flagged up for the relevant sensor $PS_J$ or group of sensors. It will be understood that, in case a plurality of proximity sensors is used, a proximity event is generally associated with an individual proximity sensor from the plurality of proximity sensors. For instance, it may very well happen that the proximity event is declared for one or more proximity sensors but not for others.

At the instant the proximity event is declared at step S660 or shortly thereafter, a new, updated, base value is chosen by signal capturing at step S680 from the relevant data stream and the so capture base value is stored in a buffer or similar.

The new base value $B_{ji}$, for an event $p_{ji}$ (for example, the first proximity event after power-up in sensor 3 would be written as $p_{30}$), may be defined as the value of $x_j$ at the beginning of the proximity event. Alternatively, at the instant of the event $p_{ji}$, the last n samples of the original signal $x_J$ are captured and the minimum capacitance value is then selected from this series of n values and this minimum is then captured as $B_{ji}$. Alternatively, a (possibly weighted) average is formed from the n captured values in the raw data stream of the respective sensor or group of sensor. For the number n of samples we have n≥1, and n depends preferably on the sensor sampling rate. Specifically, n is the larger, the higher the sampling rate is.

Returning now to the junction at step S620 and assuming a proximity event is still in effect for the relevant sensor(s), the proposed method includes a loop (up to a reasonable sampling rate) to quasi-continuously monitor at S630 the persistence of the proximity event.

That is, the declaration that the proximity event has occurred is not a one-off event but an ongoing procedure. More particularly, from the point in time the proximity event is declared, it is being (quasi-)continuously monitored (at a reasonable sampling rate) at S630 whether this event persists. Yet more particularly the capacitive values in the original data stream are now continuously monitored to detect persistent proximal presence. Till the time that the raw response signal $x_j$ fulfills a second condition, the object proximity signal remains set. Specifically and in one embodiment, the second condition is formulated as follows: Till the time that the response signal $x_j$ does not drop below $R_{ji}$ (for example, $R_{ji}=B_{ji}+S_{ji}$ and $S_{ji}=0.15\%$ of $B_{ji}$), the object proximity signal remains set. When the second condition is not fulfilled, that is, in one embodiment when the signal does drop below $R_{ji}$, the object proximity signal is reset. Said differently, at step S630 it is established whether the current raw signal $x_j$ is close to or less than the latest baseline value $B_{ji}$.

Alternatively, the same comparison is done based on the current filtered signal $y_j$. Specifically, at step S630 it is established whether a current filtered proximity signal $y_j$ still fulfills the conditions at step S640 relative to the first threshold $T_P$.

In sum, it is established at step S630 whether the previously declared proximity event is still in effect. If it is found at step S630 that the proximity event is still in effect, workflow returns to step S605 where the new proximity signal stream is received.

If, however, it is established in step S650 that the previously declared proximity event is no longer in effect, the flag is reset, that is, the proximity event is re-declared into a non-proximity event and the object approach detection system returns to a non-excited, non-proximity state. At this stage flow again returns to step S605 where the new signal readings from the proximity sensor or sensors are received.

Concurrently, whilst in proximity state, it is also established in step S670 what action (for instance a collision avoidance action), if any, is to be taken.

It should be clear from the flow chart that an action can only be taken whilst the proximity event for the relevant sensor or sensor group is in effect. In step S670 the original, raw proximity sensor signal $x_J$ or its filtered version $y_J$ is now measured against the new baseline value set at step S680. More particularly, it is established whether $x_J$ or, respectively $y_J$, as received whilst the proximity event is in effect, deviates from the new base line value by more than a pre-defined second threshold $T_C$.

The magnitude of the second threshold can be chosen so as to monitor for a non-touch event or a touch event. More particularly, at step S690 it is established whether $x_j$ or $y_J$ as the case may be, crosses the second threshold $T_C$ as measured against the new base line value. If yes, a touch or proximity signal is then issued in step S690. This signal corresponds to a request for the action to be taken in respect of the system (such as the imaging apparatus) for which the object approach scheme is used. More particularly, in one embodiment a collision avoidance action is taken. If on the other hand, the second threshold is not crossed, the flow returns to step S605 where the raw response signals continue to be received.

Alternatively, the monitoring of signal $x_J$ for touch events is achieved in the same manner that proximity events are detected. That is, if at any point while the system is in the proximity state, an excitation larger in magnitude than $T_c$ is observed in $y_J$, a touch event is declared to have occurred at the sensor J and an output signal Sb indicative of the touch event is used to effect appropriate action in the main system IA.

As explained earlier in the state diagram of FIG. 4, the method effectively oscillates between two states, the proximity state and the non-proximity state. A request for action (such as a collision avoidance action or similar) is only issued if the system method is in the object event state.

It will be understood that the above can be readily generalized to more than two events or states. That is, a hierarchy of object event states can be introduced. More particularly, rather than oscillating between a non-proximity state event and a proximity event state the system can now oscillate between a number of possibly prioritized levels of proximity events or states. In each of the proximity events of a different level, an associated new base line value is captured. In one embodiment, the action signal is then only issued if the proximity event of the highest category in that hierarchy is assumed. In another embodiment a set of different actions are assigned respectively to the different proximity levels and the respective actions associated with those levels are only executed if the proximity event at the corresponding level is in effect. In other words, the above described methods in FIG. 3 can be cascaded out into a plurality of proximity events arranged in a hierarchy of levels.

It will also be appreciated that the above described systems and method is not necessary tied to medical-imaging applications, not even to the medical field as such. More particularly, the above described object approach system ACS and method can be applied to any work equipment with moving parts. More particularly, the invention may be used in a robotic environment for example in industrial manufacturing or in storehouse management where robots or other moving equipment is used alongside human beings and where collisions can occur. For instance, in robots, proximity sensors can be attached at suitable locations on a robotic arm, etc. Maintenance personnel who are dispatched to working close to these robots whilst the robots perform their duty can be kept safe from inadvertent collision.

Also, as will be apparent from the above description, the frequency suppression in the filter stage is directed to relative motion between the proximity sensor and objects in its surroundings. More particularly, the proximity sensors may not necessarily be attached to the moving parts themselves but may be attached for instance to certain equipment in the vicinity of the moving part or may be integrated into wearables worn by human beings themselves. For instance, the proximity sensors may be integrated into work clothes or may be worn as patches etc. on exposed parts of the human body that are more prone to collision with moving parts of the surrounding working equipment. For instance, proximity sensors may be inserted in headwear or vests or other garments. The proximity sensor readings or responses are then, for instance, wirelessly forwarded by a transmitter worn by the human to the respective collision avoidance unit ACU as explained above.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular, but not necessarily, a non-transitory medium), such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An object approach detection apparatus (ACU), comprising:
    an input interface (IN) for receiving a response signal from at least one proximity sensor (PSj) measured relative to a first base-value of said at least one sensor;
    a filter module (FM) configured to filter said response signal to reduce one or more frequencies in the response signal due to the at least one proximity sensor and the object passing each other in relative motion to produce a filtered response signal;
    a proximity event declarator (PED) configured to declare a proximity event has occurred if the filtered response signal crosses a first threshold; and
    a base value adaptor (BVA) configured to choose a new base value in response of the declaring that the proximity event has occurred.

2. The apparatus of claim 1, comprising:
an action module configured to issue an output signal for an object approach action to be taken if the response signal or the filtered response signal crosses a second threshold as measured relative to said new base value.

3. The apparatus of claim 1, wherein said response signal is received whilst there is relative motion between the at least one proximity sensor (PSj) and at least one object.

4. The apparatus of claim 1, wherein the new base value corresponds to an unfiltered response signal captured at the instance of the proximity event.

5. The apparatus of claim 1, wherein the filter module is a high-pass or band-pass filter.

6. The apparatus of claim 1, wherein the proximity event declarator is configured to monitor said response signal or the filtered response signal and to re-declare the proximity event into a non-proximity event if the filtered response signal crosses the first threshold again.

7. The apparatus of claim 6, wherein the at least one proximity sensor is mounted on a movable part of a medical imaging apparatus.

8. An imaging system comprising:
an imaging apparatus;
the object approach detection apparatus of claim 1; and
one or more of the proximity sensors from which the response signal is received.

9. The image processing system of claim 8, wherein the one or more proximity sensors is arranged on a movable part of the imaging apparatus.

10. The apparatus of claim 2, wherein the action module is configured to issue said output signal only if the proximity event is declared.

11. A method of object approach detection, comprising:
receiving a response signal from at least one proximity sensor measured relative to a first base-value of said at least one sensor;
filtering said response signal by reducing one or more frequencies in said response signal that are due to the at least one proximity sensor and an object passing each other in relative motion, so as to produce a filtered response signal;
declaring a proximity event has occurred if the filtered response signal crosses a first threshold,
choosing a new base value in response of the declaring that the proximity event has occurred.

12. The method of claim 11, comprising:
issuing an output signal for an object approach action to be taken if the response signal or the filtered sensor signal crosses a second threshold as measured relative to said new base value.

13. A computer program element configured to perform the method of claim 12 on a processing unit.

14. A computer readable medium having stored thereon software configured to control a computer processor to perform the method of claim 12.

15. A computer processor configured to perform the method of claim 12.

* * * * *